United States Patent
Ooyama et al.

(10) Patent No.: US 8,163,962 B2
(45) Date of Patent: Apr. 24, 2012

(54) METHOD FOR PRODUCING ALKOXYINDANONE DERIVATIVE

(75) Inventors: Tetsuya Ooyama, Minamisouma (JP); Takashi Onozawa, Minamisouma (JP); Shin Ikeda, Minamisouma (JP); Yoshinobu Suzuki, Minamisouma (JP)

(73) Assignee: DNP Fine Chemicals Fukushima Co., Ltd., Fukushima (JP)

( * ) Notice: Subject to any disclaimer, the term of this patent is extended or adjusted under 35 U.S.C. 154(b) by 38 days.

(21) Appl. No.: 12/742,873

(22) PCT Filed: Nov. 14, 2008

(86) PCT No.: PCT/JP2008/070731
§ 371 (c)(1),
(2), (4) Date: May 13, 2010

(87) PCT Pub. No.: WO2009/063960
PCT Pub. Date: May 22, 2009

(65) Prior Publication Data
US 2010/0261935 A1    Oct. 14, 2010

(30) Foreign Application Priority Data

Nov. 14, 2007  (JP) ................. 2007-295877

(51) Int. Cl.
*C07C 45/61*    (2006.01)
(52) U.S. Cl. ........................................ 568/319
(58) Field of Classification Search ............. 568/319
See application file for complete search history.

(56) References Cited

U.S. PATENT DOCUMENTS

| 4,505,932 A | 3/1985 | DeBernardis et al. |
| 6,433,228 B1 | 8/2002 | Komoschinski et al. |

FOREIGN PATENT DOCUMENTS

| JP | 59-212430 A | 12/1984 |
| JP | 11-092427 A | 4/1999 |
| JP | 11-302216 A | 11/1999 |
| JP | 2001-514158 A | 9/2001 |

OTHER PUBLICATIONS

John Koo, "Studies in Polyphosphoric Acid Cyclizations", J. Am. Chem. Soc., 1953, pp. 1891-1895, vol. 75, No. 8.

*Primary Examiner* — Sikarl Witherspoon
(74) *Attorney, Agent, or Firm* — Sughrue Mion, PLLC

(57) ABSTRACT

[Problems to be Solved]
The present invention aims to provide a method for efficiently producing a high-purity alkoxyindanone derivative while maintaining an industrially superior volumetric efficiency.
[Solution]
Provided is a method for producing an alkoxyindanone derivative represented by a general formula in FIG. 2 (wherein R represents an alkoxy group containing 1 to 6 carbon atoms and n represents an integer of 1 to 4), comprising reacting an alkoxyphenylpropionic acid derivative represented by a general formula in FIG. 1 (wherein R and n are as defined above) with a condensing agent, adding an organic solvent to the resulting reaction mixture, and subsequently decomposing the condensing agent with an aqueous alkaline solution.

18 Claims, 5 Drawing Sheets

Fig. 4

| | Content of Self-Condensed Dimer Contained in Crude Product | Content of Self-Condensed Dimer Contained in Purified Product |
|---|---|---|
| Reference Example 1 | 2.58% | 2.42% |
| Reference Example 2 | 0.90% | 0.50% |
| Reference Example 3 | 0.19% | 0.08% |
| Reference Example 4 | 0.03% | trace |

Fig. 5

| | Condition for Decomposition of Polyphosphoric Acid | | Result of Extraction |
|---|---|---|---|
| | Concentration of NaOH (wt%) | Amount of Water or Aqueous Solution of NaOH (mL) | Distribution Ratio |
| Reference Example 5 | 0 | 40 | 0.69 |
| Reference Example 6 | 17.5 | 31 | 113 |
| Reference Example 7 | 25 | 31 | 611 |

METHOD FOR PRODUCING ALKOXYINDANONE DERIVATIVE

CROSS REFERENCE TO RELATED APPLICATIONS

This application is a National Stage of International Application No. PCT/JP2008/070731 filed Nov. 14, 2008, claiming priority based on Japanese Patent Application No. 2007-295877, filed Nov. 14, 2007, the contents of all of which are incorporated herein by reference in their entirety.

TECHNICAL FIELD

The present invention relates to an industrially advantageous method for producing a high-purity alkoxyindanone derivative using an alkoxyphenylpropionic acid derivative as a raw material. The alkoxyindanone derivative obtained by the present invention is a useful compound as a production intermediate of donepezil hydrochloride, which is a therapeutic agent for dementia and Alzheimer's disease.

BACKGROUND ART

While various reports have been made so far on a laboratory-scale method for synthesizing an alkoxyindanone derivative, there have been very few reports regarding its industrial production method.

For example, Non-Patent Document 1 discloses that 1 g of 3-(3,4-dimethoxyphenyl)propionic acid and 10 g of polyphosphoric acid were reacted at 65° C. for 25 minutes, followed by addition of cold water. Then, the resulting mixture was extracted with diethyl ether or ethyl acetate, and the organic layer thus extracted was washed with a 10% aqueous solution of sodium bicarbonate and purified by crystallization with ethanol to give 0.812 g (yield 90%) of 5,6-dimethoxy-1-indanone. However, it is also reported that the yield dropped to 71% when the reaction time was extended to 70 minutes in the above method. Generally, each unit operation is time-consuming in an industrial-scale production, and thus, it is difficult to perform operations in such a way that reactions are completed within only several tens of minutes. In view of the foregoing, the method described in the above document is far from an industrially efficient production method.

Further, Patent Document 1 discloses that 300 g of 3-(3,4-dimethoxyphenyl)propionic acid and 1500 g of polyphosphoric acid were reacted at 65° C. for 30 minutes under a nitrogen atmosphere. The reaction mixture was then cooled, to which 2000 mL of deionized water was then gradually added. The mixture was then stirred at room temperature for two hours and then extracted with 600 mL of chloroform six times. The organic layer thus extracted was washed with a saturated aqueous solution of sodium bicarbonate and dried over anhydrous magnesium sulfate, and then filtrated. The filtrate thus obtained was concentrated to dryness under reduced pressure to give 170 g (yield 62%) of 5,6-dimethoxy-1-indanone. However, in this method, a reaction vessel of approximately 3 L or larger is needed to obtain only 170 g of a target compound. Therefore, the volumetric efficiency is low. Also, industrialization of the above method is difficult because chloroform, which is highly toxic to human bodies and the environment, is used as an extraction solvent.

Further, Patent Document 2 discloses that 3-chloropropionyl chloride was reacted with 1,2-dimethoxybenzene in the presence of aluminum chloride to produce 3-chloro-3',4'-dimethoxypropiophenone in situ. To the reaction mixture concentrated sulfuric acid was added and the reaction was allowed to proceed at 70° C. The resulting product was then purified by silica gel column chromatography to give 5,6-dimethoxy-1-indanone with a yield of 40%. However, silica gel chromatography as used in the above method is a cumbersome method, and further, a problem of the above method is low yield.

According to Non-Patent Document 2, it is known that a method for producing an alkoxy compound using polyphosphoric acid as disclosed in Non-Patent Document 1 and Patent Document 1 is advantageous in that it does not cause a dealkylation reaction compared to a production method using aluminum chloride as disclosed in Patent Document 2. Accordingly, polyphosphoric acid is effective in order to obtain a quality alkoxyindanone derivative. However, as described above, a high yield cannot be anticipated unless the reaction time is as short as 25 to 30 minutes and a large amount of water is needed for decomposition of polyphosphoric acid, and also a large amount of highly toxic organic solvents is needed for extraction in the above method. Therefore, because facilities to be used and operational processes are increased when the production is carried out on an industrial scale by a conventional method, there are demerits that the production efficiency is low and large amounts of organic waste liquid and acid waste liquid are produced.

Non-Patent Document 1: J. Koo, J. Am. Chem. Soc., 75, 1891-1895 (1953)

Patent Document 1: JP Patent Publication (Kokai) No. 11-92427A (1999)

Patent Document 2: JP Patent Publication (Kokai) No. 11-302216A (1999)

Non-Patent Document 2: Edited by The Chemical Society of Japan, Experimental Chemistry, Vol. 18, a reaction of organic compounds II (the second half of the volume), 205-289 (1958)

DISCLOSURE OF THE INVENTION

Problems to be Solved by the Invention

The present inventors conducted a study on a method for producing an alkoxyindanone derivative represented by a general formula in FIG. 2 (wherein R represents an alkoxy group containing 1 to 6 carbon atoms and n represents an integer of 1 to 4) on an industrial scale by reacting an alkoxyphenylpropionic acid derivative represented by a general formula in FIG. 1 (wherein R and n are as defined above) with a condensing agent. As a result, they found the presence of an impurity that markedly affected the yield and the quality of the alkoxyindanone derivative.

As a result of isolation and structural analysis of the impurity, it was found to be a self-condensed dimer of an alkoxyindanone derivative represented by a general formula in FIG. 3 (wherein R and n are as defined above). The self-condensed dimer is considered to be produced as a result of an aldol condensation reaction of the alkoxyindanone derivative due to acid. The alkoxyindanone derivative containing a large amount of impurity as described above is not preferable because when such alkoxyindanone derivative is used as a raw material for a medicine, the alkoxyindanone derivative itself becomes an impurity in the medicine or a cause of the production of another impurity. Removal of the self-condensed dimer is considered as means for solving this problem. However, repeating purification such as recrystallization and silica gel column chromatography results in a reduced yield, namely, reduced production efficiency. Further, the operations of purification as described above become a cause of the production of a large amount of organic waste liquid and used silica gel waste. Accordingly, an industrially superior method for producing an alkoxyindanone derivative, which inhibits the production of the self-condensed dimer and which does not require excessive operations of purification, is demanded.

In Non-Patent Document 2, it is disclosed that 2-(1'-indanylidene)indanone, which is a self-condensed dimer of indanone, is produced in abundance as by-products, along with indanone, by a reaction of β-phenylpropionic acid and fluorosulfonic acid. However, the document does not discuss a method for inhibiting the production of such self-condensed dimer. Generally, the reaction rate of an aldol condensation reaction becomes fast as the concentration of the substrate and the temperature in the reaction are high. Accordingly, it is postulated that carrying out a reaction at the lowest temperature possible under the condition of low substrate concentration is effective as a method for inhibiting the production of a self-condensed dimer of an alkoxyindanone derivative. However, lowering the substrate concentration is directly linked to a reduction in the volumetric efficiency in an industrial-scale production; therefore, it is undesirable. Also, because a condensing agent such as polyphosphoric acid releases a large amount of heat upon decomposition, control of the inside temperature is difficult. Furthermore, the viscosity of the reaction liquid increases when it is cooled, by which the heat-transfer rate of the reaction vessel is markedly decreased. Thus, simple use of a cold refrigerant cannot solve the above problem. Accordingly, it is difficult to efficiently produce a high-purity alkoxyindanone derivative on an industrial scale by a conventional method.

A tremendous amount of heat is emitted when a condensing agent such as polyphosphoric acid is decomposed, and in a conventional method, the condensing agent is decomposed while adding a large amount of water to the reaction mixture containing the condensing agent. Addition of a large amount water (for example, approximately seven times based on the polyphosphoric acid in terms of volume ratio) can control elevation of the temperature of the reaction mixture because water itself absorbs heat. However, it is not an industrially superior method because addition of a large amount of water reduces the volumetric efficiency.

Also, in order to improve the volumetric efficiency, a high distribution ratio (the concentration of the alkoxyindanone derivative in an organic layer/the concentration of the alkoxyindanone derivative in an aqueous layer) is desirable when the solvent extraction is carried out after the reaction. Although neutralization of the condensing agent is effective to improve the distribution ratio, it will be a factor to make temperature control difficult because neutralization is exothermic. That is, in order to produce a high-purity alkoxyindanone derivative on an industrial scale, a production method by which easy temperature control and high volumetric efficiency can be both achieved is necessary.

In view of the foregoing, the present inventors conducted an intensive study. As a result, they have figured out that the amount of self-condensed dimer produced depends on the reaction temperature and the temperature at which the condensing agent is decomposed, and found that the content of self-condensed dimer in the alkoxyindanone derivative obtained can be reduced by controlling the above temperatures within a certain range.

Means for Solving the Problems

The present inventors have surprisingly found that temperature control of a reaction mixture while maintaining an industrially advantageous volumetric efficiency can easily be made by the following steps: reacting an alkoxyphenylpropionic acid derivatives with a condensing agent; increasing the area of heat-transfer surface by addition of an organic solvent to the resulting reaction mixture; and decomposing the condensing agent with an aqueous alkaline solution; and thereby the amount of a self-condensed dimer of an alkoxyindanone derivative can be considerably reduced compared to a conventional method.

That is, the present invention is as follows.

[1] A method for producing an alkoxyindanone derivative represented by a general formula in FIG. 2 (wherein R represents an alkoxy group containing 1 to 6 carbon atoms and n represents an integer of 1 to 4), comprising: reacting an alkoxyphenylpropionic acid derivative represented by a general formula in FIG. 1 (wherein R and n are as defined as above) with a condensing agent; adding an organic solvent to the resulting reaction mixture; and decomposing the condensing agent with an aqueous alkaline solution.

[2] A method for producing an alkoxyindanone derivative represented by a general formula in FIG. 2 (wherein R represents an alkoxy group containing 1 to 6 carbon atoms and n represents an integer of 1 to 4), comprising: reacting an alkoxyphenylpropionic acid derivative represented by a general formula in FIG. 1 (wherein R and n are as defined as above) with a condensing agent; adding an organic solvent to the resulting reaction mixture; while decomposing the condensing agent with an aqueous alkaline solution, extracting a reaction product with the organic solvent; and purifying the reaction product by crystallization using the same organic solvent as the extraction solvent.

[3] A method for producing an alkoxyindanone derivative represented by a general formula in FIG. 2 (wherein R represents an alkoxy group containing 1 to 6 carbon atoms and n represents an integer of 1 to 4), comprising: reacting an alkoxyphenylpropionic acid derivative represented by a general formula in FIG. 1 (wherein R and n are as defined as above) with a condensing agent; adding an organic solvent to the resulting reaction mixture; while decomposing the condensing agent with an aqueous alkaline solution, extracting a reaction product with the organic solvent; removing by-products by washing an organic layer containing the extracted reaction product with the aqueous alkaline solution; and purifying the reaction product by crystallization using the same organic solvent the extraction solvent.

[4] The method for producing an alkoxyindanone derivative according to any of the above-described [1] to [3], wherein the amount of the condensing agent used is 2 to 10 times based on the alkoxyphenylpropionic acid derivative in terms of weight ratio.

[5] The method for producing an alkoxyindanone derivative according to any of the above-described [1] to [4], wherein the temperature of the reaction of the alkoxyphenylpropionic acid derivative with the condensing agent is 0 to 70° C.

[6] The method for producing an alkoxyindanone derivative according to any of the above-described [1] to [5], wherein the decomposition temperature of the condensing agent is 0 to 70° C.

[7] The method for producing an alkoxyindanone derivative according to any of the above-described [1] to [6], wherein the condensing agent is a polyphosphoric acid.

[8] The method for producing an alkoxyindanone derivative according to any of the above-described [1] to [7], wherein the organic solvent is an aromatic hydrocarbon.

Advantages of the Invention

According to the present invention, a high-purity alkoxyindanone derivative can be efficiently produced while maintaining an industrially superior volumetric efficiency.

BEST MODE FOR CARRYING OUT THE INVENTION

Hereinbelow, the best embodiment of the present invention (hereinbelow, the present embodiment) will be described in detail. It is to be noted that the present invention is not limited to the following embodiment and can be practiced in various modified forms without departing from the scope of the invention.

The method for producing an alkoxyindanone derivative of the present embodiment is a method in which an alkoxyphenylpropionic acid derivative represented by a general formula in FIG. 1 is reacted with a condensing agent, an organic solvent is subsequently added to the resulting reaction mixture, and the condensing agent is decomposed with an aqueous alkaline solution.

Examples of an alkoxy group having 1 to 6 carbon atoms represented by R in general formulae in FIG. 1, FIG. 2, and FIG. 3 include methoxy group, ethoxy group, n-propoxy group, isopropoxy group, n-butoxy group, isobutoxy group, sec-butoxy group, tert-butoxy group, n-pentyloxy group, isopentyloxy group, sec-pentyloxy group, n-hexyloxy group, isohexyloxy group, 1,1-dimethylpropoxy group, 1,2-dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, and 3-methylpentyloxy group. Among them, methoxy group, ethoxy group, n-propoxy group, and isopropoxy group are preferred, among which methoxy group and ethoxy group are more preferred.

According to the production method of the present embodiment, in a method for producing an alkoxyindanone derivative represented by a general formula in FIG. 2 by reacting an alkoxyphenylpropionic acid derivative represented by a general formula in FIG. 1 with a condensing agent, an organic solvent is added to the reaction mixture so that the area of heat-transfer surface is increased before the condensing agent is decomposed. By doing so, the cooling efficiency is improved and it is made possible to easily control the temperature at which the condensing agent is decomposed within the range of 0 to 70° C. Consequently, the production of a self-condensed dimer of an alkoxyindanone derivative represented by a general formula in FIG. 3 is inhibited.

As an organic solvent to be added to the reaction mixture, aromatic hydrocarbon is preferred, among which toluene is preferred because the distribution ratio in the extraction process that will be described later tends to be favorable.

Also, in the production method of the present embodiment, an aqueous alkaline solution is added to the reaction mixture after completion of the reaction to decompose a condensing agent, and by doing so, the aqueous alkaline solution reduces the acidity of the condensing agent. The above procedure could further inhibit the production of a self-condensed dimer of an alkoxyindanone derivative represented by a general formula in FIG. 3.

Furthermore, because a conventional method uses water to decompose a condensing agent to obtain a sufficiently large distribution ratio in the extraction of an alkoxyindanone derivative, water has been needed in an amount twice or more the amount of the condensing agent used in terms of volume ratio. However, an aqueous alkaline solution is used instead of water in the production method of the present embodiment. Therefore, a sufficiently large distribution ratio can be obtained in the extraction of an alkoxyindanone derivative by using the aqueous alkaline solution in an amount equal to or less than the amount of the condensing agent used in terms of volume ratio. Accordingly, because the volume of the solution required for extraction of the alkoxyindanone derivative is considerably reduced, the volumetric efficiency of the reaction vessel can be improved and yield per batch is increased, by which the production efficiency can be improved. Furthermore, there is another merit that the amount of an acid waste liquid discharged can be considerably reduced.

While no limitation is imposed on the aqueous alkaline solution to be used for decomposition of a condensing agent, an aqueous solution of sodium hydroxide and an aqueous solution of potassium hydroxide are preferred because they are inexpensive.

While no limitation is imposed on the concentration of the aqueous alkaline solution to be used for decomposition of a condensing agent, it is preferably 10 to 50 wt %, and more preferably 15 to 30 wt %. There is a risk of reduction in the distribution ratio in the extraction when the amount of the aqueous alkaline solution used is equal to or less than the amount of the condensing agent used in terms of volume ratio and the concentration of the aqueous alkaline solution is less than 10 wt %.

The aqueous alkaline solution to be used for decomposition of a condensing agent is not necessarily prepared to have a desired concentration prior to use. Water can be added to a solution upon completion of a reaction and then an aqueous alkaline solution or solid alkali can be added to the resulting aqueous solution so that the solution can achieve a desired concentration.

While the amount of the aqueous alkaline solution to be used for decomposition of a condensing agent can be varied depending on the kind of the alkali and the concentration, it is preferably 0.3 to 2 times, more preferably 0.4 to 1.25 times the amount of the condensing agent used in terms of volume ratio.

The decomposition temperature of a condensing agent is preferably 0 to 70° C., and more preferably 30 to 60° C. When the decomposition temperature is below 0° C., the distribution ratio in the extraction is reduced. For this, the amount of an organic solvent used is increased and the volumetric efficiency tends to be decreased. When the above temperature exceeds 70° C., the production of a self-condensed dimer of an alkoxyindanone derivative is increased and the purity of the target compound tends to be reduced.

Examples of the condensing agent used in the production method of the present embodiment include, but are not particularly limited to, polyphosphoric acid, ethyl ester of polyphosphoric acid obtained by phosphorus pentoxide and diethyl ether, a mixture of phosphorus pentoxide and methanesulfonic acid, a mixture of polyphosphoric acid and phosphorus oxychloride, a mixture of phosphorus pentoxide and dimethyl sulfoxide, a mixture of phosphorus pentoxide and sulfuric acid, and a mixture of phosphorus pentoxide and tertiary amine. Among them, polyphosphoric acid is preferred because it is inexpensive and industrially easily obtainable.

Examples of polyphosphoric acid include, but are not particularly limited to, polyphosphoric acid having the phosphoric acid concentration of 95 to 125 wt %, more preferably 105 to 125 wt %, and further preferably 110 to 117 wt %. When the phosphoric acid concentration is lower than 95 wt %, its activity as a condensing agent is reduced, and thus the progress of reaction tends to be slowed down. When the phosphoric acid concentration is higher than 125 wt %, the viscosity becomes too high and handling tends to be difficult. When the phosphoric acid concentration is 105 to 125 wt %, the reaction proceeds moderately and handling tends to be easy. Therefore, the above-described phosphoric acid concentration is preferred.

The polyphosphoric acid can be prepared during the production process of the alkoxyindanone derivative. For example, a polyphosphoric acid prepared by mixing commercial phosphoric acid and phosphorus pentoxide or by dehydrating phosphoric acid with heat can be used.

Also, as polyphosphoric acid, a commercial product can be used. For example, polyphosphoric acid manufactured by Wako Pure Chemical Industries, Ltd can be used.

The amount of a condensing agent used is 2 to 10 times, and more preferably 4 to 7 times based on the alkoxyphenylpropionic acid derivative in terms of weight ratio. When the amount of a condensing agent used exceeds the above-described ranges, a large amount of aqueous alkaline solution will be needed for decomposition of the condensing agent after completion of the reaction. Therefore, the volumetric efficiency tends to be reduced. On the other hand, when the amount of a condensing agent used is below the above-described ranges, the amount of a self-condensed dimer of an alkoxyindanone derivative is increased. Therefore, the purity of the target compound tends to be reduced.

The temperature of the reaction of an alkoxyphenylpropionic acid derivative with a condensing agent is preferably 0 to 70° C., and more preferably 40 to 60° C. When the reaction temperature is below 0° C., the progress of reaction tends to be slowed down. In contrast, when the reaction temperature exceeds 70° C., the production of a self-condensed dimer of an alkoxyindanone derivative is increased, and the purity of the target compound tends to be reduced.

The reaction time of an alkoxyphenylpropionic acid derivative with a condensing agent can be appropriately varied depending on the reaction temperature. However, it is preferably 0.5 to 10 hours, and more preferably 0.5 to 2 hours.

Further, the method for producing an alkoxyindanone of the present embodiment can be performed by reacting an alkoxyphenylpropionic acid derivative represented by a general formula in FIG. 1 with a condensing agent, after which an organic solvent is added to the resulting reaction mixture, and then while decomposing the condensing agent with an aqueous alkaline solution, extracting a reaction product with the organic solvent, and then purifying the reaction product by crystallization using the same organic solvent as the extraction solvent.

By extracting an alkoxyindanone derivative, which is the reaction product, with an organic solvent while decomposing a condensing agent, the reaction of the alkoxyindanone derivative with the condensing agent can be inhibited. Therefore, the production of a self-condensed dimer of an alkoxyindanone derivatives can be further inhibited. The number of extraction is preferably 1 to 5, and more preferably 2 to 3, but it is not particularly limited thereto.

Further, in the production method of the present embodiment, by washing the organic layer containing the extracted reaction product with an aqueous alkaline solution as needed, the reaction product can be purified as by-products and residual raw materials are removed. At this point, examples of the aqueous alkaline solution used include, but are not particularly limited to, an aqueous solution of sodium hydroxide and an aqueous solution of potassium hydroxide.

The concentration of an aqueous alkaline solution used to wash the organic layer is preferably 3 to 50 wt %, and more preferably 3 to 25 wt %. When the concentration of an aqueous alkaline solution is less than 3 wt %, there is a risk that the impurity may not be sufficiently removed.

Furthermore, the organic layer that has been washed with an aqueous alkaline solution can further be washed with water or saline, and an operation to remove any alkali or a salt thereof remaining in the organic layer can be performed.

Moreover, in the production method of the present embodiment, after the above-described extraction process, the alkoxyindanone derivative can be purified by crystallization using the same organic solvent as the extraction solvent. By using the same organic solvent, facilities to be used and operational processes can be reduced and the production efficiency can be improved. Furthermore, because two or more organic solvents are not mixed, the used organic layer can be easily recycled after purification by distillation. Therefore, the amount of an organic waste liquid discharged can be considerably reduced.

Examples of the method of purification by crystallization that can be employed include a method in which the organic solvent in the extracted organic layer is distilled off and an alkoxyindanone derivative is crystallized, either after or while concentrating the organic layer. When the extracted organic layer is concentrated, it is concentrated until the organic solvent remaining in the residual organic layer after distillation is 1 to 10 times, preferably 1 to 3 times based on the crude product of the alkoxyindanone derivative contained in the extracted organic layer in terms of volume ratio, whereby the alkoxyindanone derivative is crystallized out. When the amount of the organic solvent remaining in the residual organic layer exceeds three times based on the crude product, there is a risk that the yield might be low. When the amount of the organic solvent remaining in the residual organic layer is less than the amount of the crude product, the organic layer may lack fluidity as slurry, which might make handling difficult.

Furthermore, in purification by crystallization, an adsorbent can be added as needed and crystallization can be carried out after filtering the adsorbent out. Examples of the adsorbent that can be used include, but are not particularly limited to, activated carbon, activated clay, Japanese acid clay, silica gel, and alumina gel.

The crystallization temperature is preferably −10 to 40° C., and more preferably −5 to 15° C. When the temperature is below −5° C., there is a risk that the purity of the target compound might be reduced. When the temperature exceeds 15° C., there is a risk that the yield of the target compound might be reduced.

In the present embodiment, a starting material to be used is an alkoxyphenylpropionic acid derivative represented by a general formula in FIG. 1 (wherein R represents an alkoxy group containing 1 to 6 carbon atoms, and n represents an integer of 1 to 4). A commercial product of the above-described compound can be directly used, or the above-described compound can also be produced by a known method from a commercial product. Examples of the commercial product that can be used include 3-(3,4-dimethoxyphenyl) propionic acid manufactured by Tokyo Chemical Industry, Co., Ltd.

The alkoxyindanone derivative obtainable by the present invention can be converted to donepezil hydrochloride, which is useful as a therapeutic agent for dementia and Alzheimer's disease, by a method known per se as described in JP Patent No. 2578475.

EXAMPLES

The present embodiment is described in detail with Examples shown hereinbelow.

Example 1

To a 2 L 4-necked flask having a condenser, a calcium chloride tube, a nitrogen-introducing tube, a mechanical stirrer, and a thermometer, 450 g of 85% phosphoric acid was added under a nitrogen stream and stirring was initiated. To this flask, 550 g of phosphorus pentoxide was gradually added, and the mixture was stirred at 120° C. to prepare 1000 g of polyphosphoric acid. After stirring for one hour, the polyphosphoric acid was cooled to 40° C. and 200 g of 3-(3, 4-dimethoxyphenyl)propionic acid (manufactured by Tokyo Chemical Industry, Co., Ltd.) was added, followed by stirring at 60° C. After stirring for two hours, the mixture was cooled to 40° C., and 435 g of toluene was added, and the mixture was further cooled to 30° C. Subsequently, 282 g of water and 657 g of a 25% aqueous solution of sodium hydroxide were added dropwise while maintaining the temperature at 70° C. or lower, and extraction was performed while the condensing agent is decomposed, thereby the organic layer was separated. Into the separated aqueous layer, 435 g of toluene was added and the mixture was heated to 50° C. and extraction was repeated. The organic layer was separated and transferred to another 2 L 4-necked flask. The two organic layers thus obtained were combined and washed with 210 g of a 5% aqueous solution of sodium hydroxide. The organic layer was further washed with 10% saline and water. A crude product of 5,6-dimethoxy-1-indanone was sampled from the washed organic layer and analyzed by HPLC. As a result, the purity was 99.55% and the content of the self-condensed dimer was 0.01%. The organic layer thus obtained was subjected to distillation under reduced pressure, and toluene was distilled off until the amount of the liquid was approximately 730 mL. In the concentrated liquid thus obtained, 2 g of activated carbon was added. The liquid was heated to 65° C. and stirred for 30 minutes. Subsequently, the liquid was filtrated to remove the activated carbon. Further, the obtained filtrate was subjected to distillation, and toluene was distilled off until the amount of the liquid was approximately 370 mL, whereby 5,6-dimethoxy-1-indanone was crystallized out. Further, 5,6-dimethoxy-1-indanone was crystallized out by cooling the liquid to 5° C. in an ice water bath. The liquid was filtrated and the crystal thus obtained was dried. As a result, 159.5 g (yield 87%) of purified crystal of 5,6-dimethoxy-1-indanone was obtained as light yellow crystalline powder. The purified product of 5,6-dimethoxy-1-indanone thus obtained was analyzed by HPLC, and it was found that the purity was 99.99% or higher and the amount of the self-condensed dimer contained was 0.01% or less. Conditions of HPLC: detector: ultraviolet absorption spectrometer (measurement wavelength: 242 nm), column: Inertsil ODS-3 (diameter of 4.6 mm×250 mm), mobile phase: acetonitrile/methanol=4/6, flow rate: 1.0 mL/min, column temperature: 40° C.

Comparative Example 1

To a 5 L 4-necked flask having a condenser, a calcium chloride tube, a mechanical stirrer, and a thermometer, 1002 g of polyphosphoric acid (manufactured by Wako Pure Chemical Industries, Ltd.) was added and stirring was initiated. To this flask, 200 g of 3-(3,4-dimethoxyphenyl)propionic acid was added, and the mixture was stirred at 65° C. After stirring for 30 minutes, the mixture was cooled to 30° C. and dropwise addition of 2500 mL of cold water of 7° C. was initiated. When approximately 300 mL of cold water had been added dropwise, the temperature of the mixture abruptly rose to 87° C. Subsequently, the mixture was cooled, and cold water was added dropwise so that the temperature was maintained at 70° C. or lower. Upon completion of dropwise addition of cold water, the mixture was stirred at room temperature for 30 minutes, and the reaction mixture thus obtained was transferred to a 10 L 4-necked flask. Into the flask, 2500 mL of toluene was added and the mixture was heated to 50° C., and then subjected to extraction to separate an organic layer. To the organic layer thus separated, 2500 mL of saturated aqueous solution of sodium bicarbonate was added. The mixture was heated to 50° C. and washed. The mixture was further washed with saline and water, and the organic layer thus obtained was dried over sodium sulfate, and then toluene was distilled off under reduced pressure to give solid. As a result, 168.2 g of a crude product of 5,6-dimethoxy-1-indanone was obtained as yellow solid. The crude product of 5,6-dimethoxy-1-indanone thus obtained was analyzed by HPLC. As a result, the purity was 99.81% and the content of the self-condensed dimer was 0.07%. The crude product thus obtained was then subjected to decolorization by adsorption using silica gel and activated carbon, and then recrystallized from acetone/hexane. The recrystallized product thus obtained was further recrystallized from ethanol, and the crystal thus obtained was dried to give 118 g (yield 64%) of purified crystal of 5,6-dimethoxy-1-indanone as light yellow crystalline powder. The purified product of 5,6-dimethoxy-1-indanone thus obtained was analyzed by HPLC. As a result, the purity was found to be equivalent to the purity of the purified product of 5,6-dimethoxy-1-indanone obtained in Example 1. Conditions of HPLC: detector: ultraviolet absorption spectrometer (measurement wavelength: 242 nm), column: Inertsil ODS-3 (diameter of 4.6 mm×250 mm), mobile phase: acetonitrile/methanol=4/6, flow rate: 1.0 mL/min, column temperature: 40° C.

Reference Examples 1-4

(1) Study on Purification of an Alkoxyindanone Derivative by Crystallization 1 g of a crude product of 5,6-dimethoxy-1-indanone containing a predetermined amount of a self-condensed dimer was purified by recrystallization from 1 mL of toluene. The purified product thus obtained was analyzed by HPLC in a similar manner to the above to determine the content of the self-condensed dimer. The contents of the self-condensed dimer in the crude and purified products of 5,6-dimethoxy-1-indanone obtained in this experiment are shown in FIG. 4.

Conditions of HPLC: detector: ultraviolet absorption spectrometer (measurement wavelength: 242 nm), column: Inertsil ODS-3 (diameter of 4.6 mm×250 mm), mobile phase: acetonitrile/methanol=4/6, flow rate: 1.0 mL/min, column temperature: 40° C.

As apparent from the results in FIG. 4, as a result of a study on purification by recrystallization with toluene, it was verified that removal of self-condensed dimer by recrystallization became difficult as the content of self-condensed dimer in the crude product was increased. The importance of inhibiting the production of self-condensed dimer in the step of the reaction of an alkoxyphenylpropionic acid derivative with a condensing agent was confirmed in the production of a high-purity alkoxyindanone derivative.

Reference Examples 5-7

(2) Relationship Between the Concentration of an Aqueous Alkaline Solution in Decomposition of a Condensing Agent and the Distribution Ratio of an Alkoxyindanone Derivative in the Extraction Into a 100 mL 4-necked flask, 40 g of polyphosphoric acid and 8 g of 3-(3,4-dimethoxyphenyl)propionic acid were added and the mixture was stirred for two hours while heating at 55 to 65° C. Upon completion of stirring, the mixture was cooled, to which a predetermined amount of water or an aqueous solution of sodium hydroxide having a predetermined concentration was added dropwise according to FIG. 5 shown below. Then, the mixture was extracted with 20 mL of toluene at a temperature of 50 to 60° C. The aqueous and organic layers separated by extraction were quantitatively analyzed by HPLC to determine distribution ratios of 5,6-dimethoxy-1-indanone in the extraction (the concentration of 5,6-dimethoxy-1-indanone in the organic layer/the concentration of 5,6-dimethoxy-1-indanone in the aqueous layer). The concentrations and amounts of aqueous solution of sodium hydroxide used and the distribution ratios of 5,6-dimethoxy-1-indanone in the extraction in this experiment are shown in FIG. 5.

Conditions of HPLC: detector: ultraviolet absorption spectrometer (measurement wavelength: 242 nm), column: Inertsil ODS-3 (diameter of 4.6 mm×250 mm), mobile phase: phosphate buffer/methanol=6/4, flow rate: 1.0 mL/min, column temperature: 40° C.

As apparent from the results in FIG. 5, it was verified that as the concentration of the aqueous alkaline solution was increased, the distribution ratio became high, and extraction became easy. That is, when decomposing a condensing agent by a conventional method using water, it has been necessary to use water in an amount several times or more the amount of the condensing agent used in terms of volume ratio. However, it was verified that, when using an aqueous alkaline solution, the distribution ratio in the extraction of an alkoxyindanone derivative could be made sufficiently high, even if the amount of the aqueous alkaline solution used was equal to or less than the amount of the condensing agent used in terms of volume ratio. Further, because the amount of extraction solvent used and the number of extraction can be reduced owing to an improved distribution ratio, the volumetric efficiency can be improved in comparison with the conventional method.

The following findings are obtained from the results of the above-described Examples, Comparative Examples, and Reference Examples. According to the production method of the present embodiment, in a method for producing an alkoxyindanone derivative by reacting an alkoxyphenylpropionic acid derivative with a condensing agent, controlling a reaction mixture at a certain temperature is made easy while maintaining an industrially superior volumetric efficiency. As a result, the amount of self-condensed dimer of an alkoxyindanone derivative produced can be suppressed to 0.03% or less as analyzed by HPLC. Further, a high-purity alkoxyindanone derivative can be efficiently produced by purifying the alkoxyindanone derivative by recrystallization from the liquid used for extraction of the derivative. The production method of the present embodiment does not require any special, expensive reagent, facility, or the like but enables efficient production of a high-purity alkoxyindanone derivative with common reagents and production facilities. Therefore, the production method is industrially extremely advantageous.

BRIEF DESCRIPTION OF THE DRAWINGS

FIG. 4 is an explanatory diagram showing that removal of self-condensed dimer by recrystallization becomes difficult as the content of self-condensed dimer in the crude product is increased.

FIG. 5 is an explanatory diagram showing that as the concentration of the aqueous alkaline solution is increased upon extraction, the distribution ratio becomes high, and extraction becomes easy.

Figure 1:
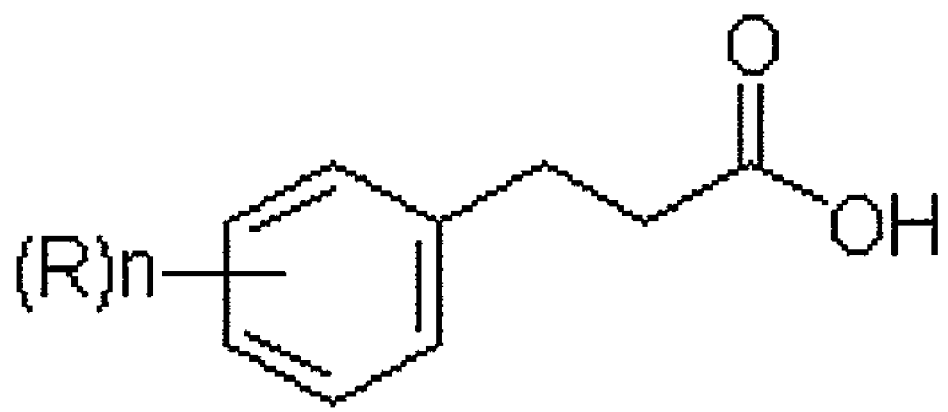
FIG. 1 is an explanatory diagram showing an alkoxyphenylpropionic acid derivative, which is a raw material.
Figure 2:
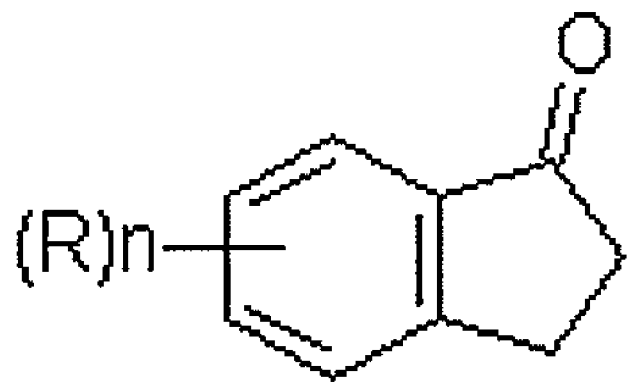
FIG. 2 is an explanatory diagram showing an alkoxyindanone derivative, which is the target compound of the present application.
Figure 3:
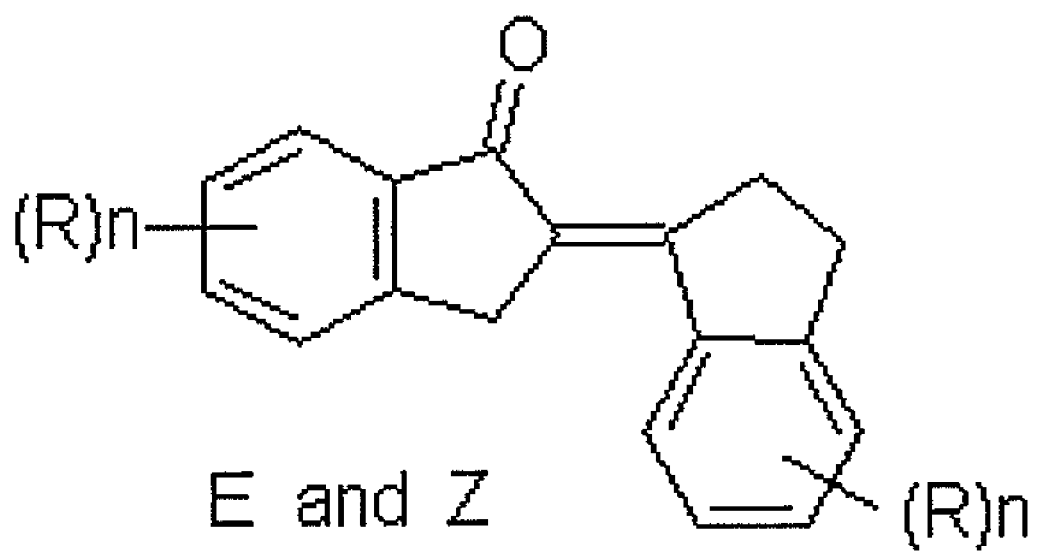
FIG. 3 is an explanatory diagram showing self-condensed dimer of an alkoxyindanone derivative, which is an impurity.

The invention claimed is:

1. A method for producing an alkoxyindanone derivative represented by a general formula:

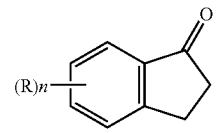

(wherein R represents an alkoxy group containing 1 to 6 carbon atoms and n represents an integer of 1 to 4), comprising, in the following order:

reacting an alkoxyphenylpropionic acid derivative represented by a general formula:

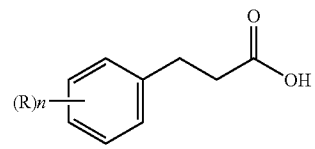

(wherein R and n are as defined above) with a condensing agent;

followed by, without any intervening steps, adding an organic solvent to the resulting reaction mixture; and decomposing the condensing agent with an aqueous alkaline solution.

2. A method for producing an alkoxyindanone derivative represented by a general formula:

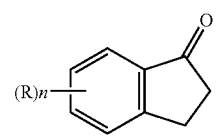

(wherein R represents an alkoxy group containing 1 to 6 carbon atoms and n represents an integer of 1 to 4), comprising, in the following order:

reacting an alkoxyphenylpropionic acid derivative represented by a general formula:

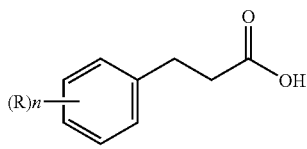

(wherein R and n are as defined above) with a condensing agent;
followed by, without any intervening steps, adding an organic solvent to the resulting reaction mixture;
while decomposing the condensing agent with an aqueous alkaline solution, extracting a reaction product with the organic solvent; and
purifying the reaction product by crystallization using the same organic solvent as the extraction solvent.

3. A method for producing an alkoxyindanone derivative represented by a general formula:

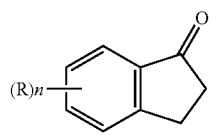

(wherein R represents an alkoxy group containing 1 to 6 carbon atoms and n represents an integer of 1 to 4), comprising, in the following order:
reacting an alkoxyphenylpropionic acid derivative represented by a general formula:

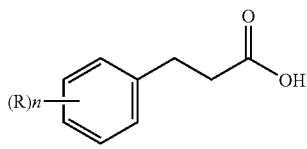

(wherein R and n are as defined above) with a condensing agent;
followed by, without any intervening steps, adding an organic solvent to the resulting reaction mixture;
while decomposing the condensing agent with an aqueous alkaline solution, extracting a reaction product with the organic solvent;
removing by-products by washing an organic layer containing the extracted reaction product with an aqueous alkaline solution; and
purifying the reaction product by crystallization using the same organic solvent as the extraction solvent.

4. The method for producing an alkoxyindanone derivative according to claim 1, wherein the amount of the condensing agent used is 2 to 10 times based on the alkoxyphenylpropionic acid derivative in terms of weight ratio.

5. The method for producing an alkoxyindanone derivative according to claim 1, wherein the temperature of the reaction of the alkoxyphenylpropionic acid derivative with the condensing agent is 0 to 70° C.

6. The method for producing an alkoxyindanone derivative according to claim 1, wherein the decomposition temperature of the condensing agent is 0 to 70° C.

7. The method for producing an alkoxyindanone derivative according to claim 1, wherein the condensing agent is a polyphosphoric acid.

8. The method for producing an alkoxyindanone derivative according to claim 1, wherein the organic solvent is an aromatic hydrocarbon.

9. The method for producing an alkoxyindanone derivative according to claim 2, wherein the amount of the condensing agent used is 2 to 10 times based on the alkoxyphenylpropionic acid derivative in terms of weight ratio.

10. The method for producing an alkoxyindanone derivative according to claim 3, wherein the amount of the condensing agent used is 2 to 10 times based on the alkoxyphenylpropionic acid derivative in terms of weight ratio.

11. The method for producing an alkoxyindanone derivative according to claim 2, wherein the temperature of the reaction of the alkoxyphenylpropionic acid derivative with the condensing agent is 0 to 70° C.

12. The method for producing an alkoxyindanone derivative according to claim 3, wherein the temperature of the reaction of the alkoxyphenylpropionic acid derivative with the condensing agent is 0 to 70° C.

13. The method for producing an alkoxyindanone derivative according to claim 2, wherein the decomposition temperature of the condensing agent is 0 to 70° C.

14. The method for producing an alkoxyindanone derivative according to claim 3, wherein the decomposition temperature of the condensing agent is 0 to 70° C.

15. The method for producing an alkoxyindanone derivative according to claim 2, wherein the condensing agent is a polyphosphoric acid.

16. The method for producing an alkoxyindanone derivative according to claim 3, wherein the condensing agent is a polyphosphoric acid.

17. The method for producing an alkoxyindanone derivative according to claim 2, wherein the organic solvent is an aromatic hydrocarbon.

18. The method for producing an alkoxyindanone derivative according to claim 3, wherein the organic solvent is an aromatic hydrocarbon.

\* \* \* \* \*